US00PP34999P2

(12) United States Plant Patent
Meier

(10) Patent No.: US PP34,999 P2
(45) Date of Patent: Feb. 21, 2023

(54) ***HAKONECHLOA* PLANT NAMED 'HAKBRI1'**

(50) Latin Name: *Hakonechloa macra*
Varietal Denomination: Hakbri1

(71) Applicant: Gurjit Sidhu, Mission (CA)

(72) Inventor: Corey Meier, Centralia, WA (US)

(73) Assignee: Gur Jit Sidhu, Mission (CA)

( * ) Notice: Subject to any disclaimer, the term of this patent is extended or adjusted under 35 U.S.C. 154(b) by 0 days.

(21) Appl. No.: 17/947,326

(22) Filed: Sep. 19, 2022

(30) Foreign Application Priority Data

Jun. 3, 2022 (CA) ..... 2210985

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
CPC ..... A01H 5/12; A01H 5/00; A01H 6/46
See application file for complete search history.

*Primary Examiner* — June Hwu
(74) *Attorney, Agent, or Firm* — Penny J. Aguirre

(57) ABSTRACT

A new and unique cultivar of *Hakonechloa* plant named 'Hakbri1' that is characterized by its variegated foliage that is chartreuse in color with yellow and creamy white stripes.

2 Drawing Sheets

Botanical classification: *Hakonechloa macra.*
Varietal designation: 'Hakbri1'.

CROSS-REFERENCE TO A RELATED APPLICATION

This application claims priority to a Canadian Plant Breeder's Rights Application No. 22-10985 filed on Jun. 3, 2022, under 35 U.S.C. 119(f), the entire contents of which is incorporated by reference herein.

BACKGROUND OF THE INVENTION

The present invention relates to a new and distinct cultivar of *Hakonechloa macra* and will be referred to hereafter by its cultivar name, 'Hakbri1'. 'Hakbri1' represents a new ornamental grass grown for landscape use.

The inventor discovered the new cultivar in spring of 2016 as a naturally occurring shoot mutation of *Hakonechloa macra* 'All Gold' (not patented) that was growing in a container in a production block in Elma, Wash.

Asexual propagation of the new cultivar was first accomplished by tissue culture using meristematic tissue in Elma, Wash. in 2017 by the Inventor. Asexual propagation by tissue culture has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Hakbri1' as a unique cultivar of *Hakonechloa.*

1. 'Hakbri1' exhibits variegated foliage that is chartreuse in color with yellow and creamy white stripes.

The female is similar to 'Hakbri1' in having foliage that is chartreuse in color. The female parent differs from 'Hakbri1' in having darker colored foliage with no variegation. 'Hakbri1' can also be compared to the *Hakonechloa macra* cultivar 'Aureola' (not patented). 'Aureola' is similar to 'Hakbri1' in having variegated foliage. 'Aureola' differs from 'Hakbri1' in having foliage that is green with stripes of yellow.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period to the filing date. Disclosures include website listings by Briggs Nursery and Babikow.

BRIEF DESCRIPTION OF THE DRAWINGS

The accompanying color photographs illustrate the overall appearance and distinct characteristics of the new *Hakonechloa*. The photographs in FIG. 1 and FIG. 2 were taken of a 3-year-old plant of 'Hakbri1' as grown outdoors in a C1 container in Elma, Wash.

The photograph in FIG. 1 provides a side view of 'Hakbri1'.

Figure 1:
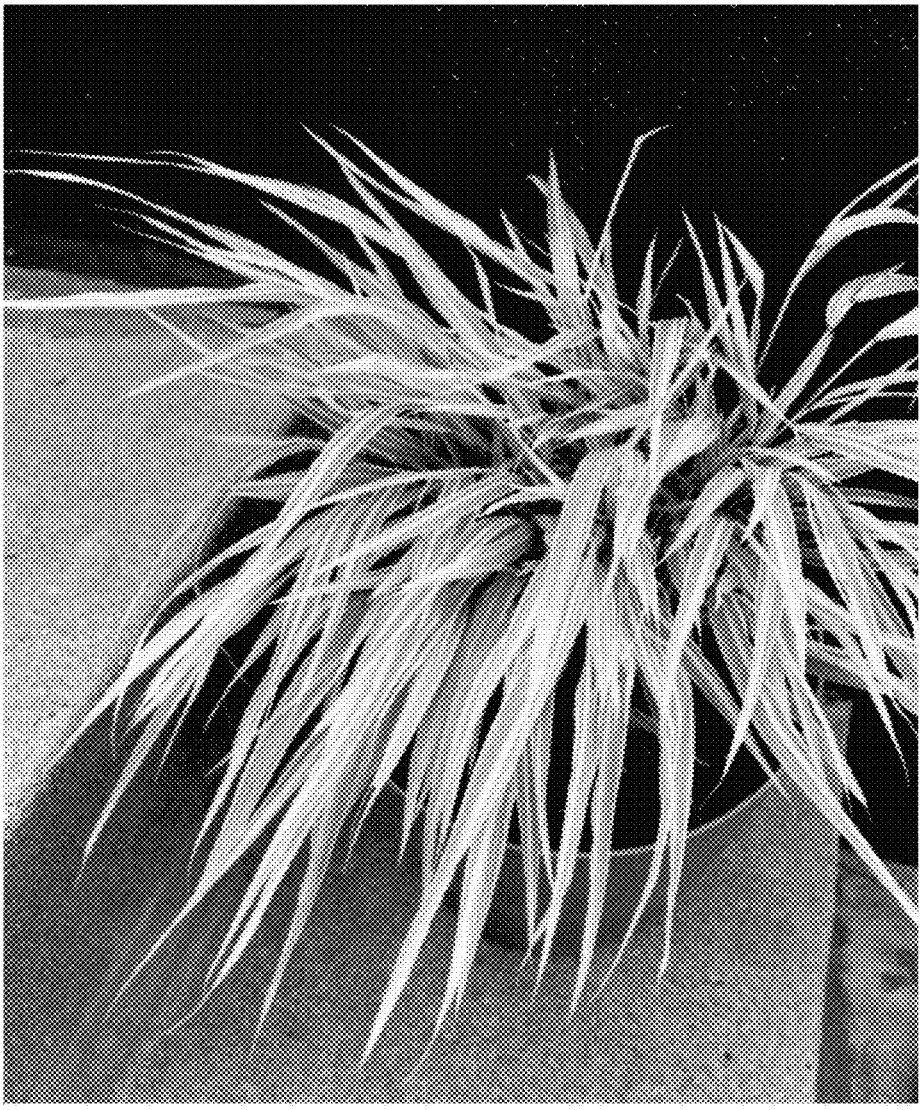
Figure 2:
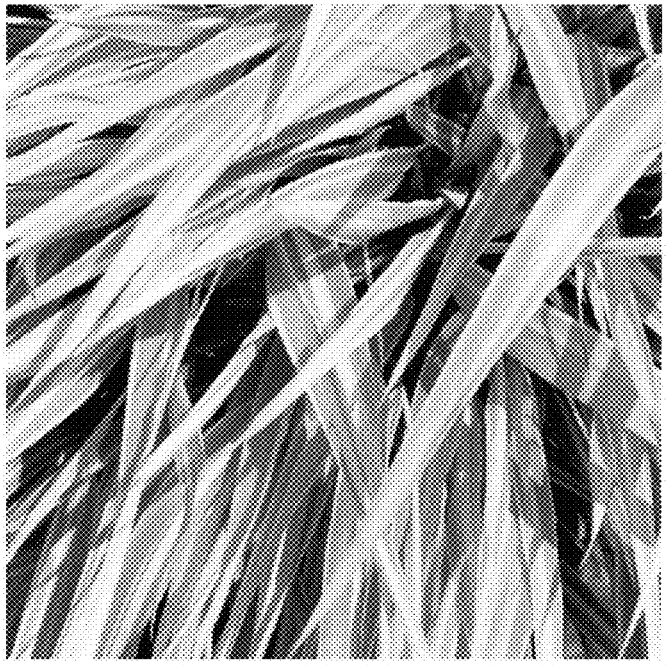

The photograph in FIG. 2 provides a close-up view of the foliage of 'Hakbri1'.

Figure 3:
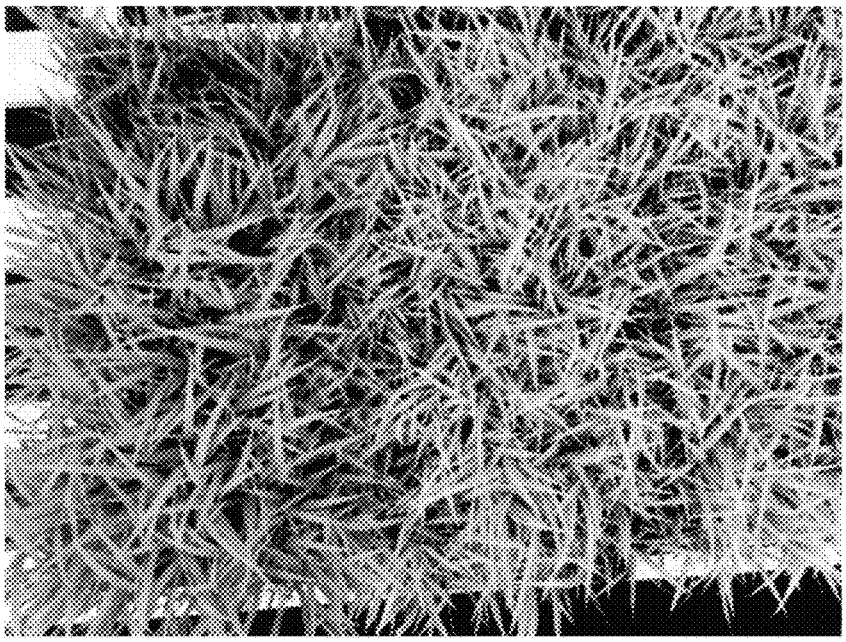

The photograph in FIG. 3 was taken of 1-year-old plants as grown in 128-cell liners in Elma, Wash. and provides a comparison between 'All Gold' (plants on left) 'Hakbri1' (plants on right).

The colors in the photographs may differ slightly from the color values cited in the detailed botanical description, which accurately describe the colors of the new *Hakonechloa.*

BOTANICAL DESCRIPTION OF THE PLANT

The following is a detailed description of 3-year-old plants of 'Hakbri1' as grown outdoors in C1 containers in Elma, Wash. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming habit*.—Late summer into early fall in Elma, Wash.

*Plant type*.—Herbaceous grass.

*Plant habit*.—Compact plant habit forming a low growing mound of cascading foliage.

*Height and spread*.—An average of 24 cm in height and spread in a one-gallon container, an average of 30 cm in height and 60 cm in width in the landscape.

*Hardiness*.—At least in U.S.D.A. Zones 5 to 9.

*Diseases and pests*.—No susceptibility or resistance to diseases or pests has been observed.

*Root description*.—Fibrous, fine, and dense, N200A in color.

*Root development*.—Average of 4 weeks for root initiation and 6 months to produce a young plant in a liner.

*Propagation*.—Tissue culture.

*Growth rate*.—Vigorous.

Culm (stem) description:

*General*.—Round, sheathed.

*Culm color*.—158B, covered by leaf sheaths; 187A.

*Culm size*.—Average of 9 cm in length and 1 mm in width.

*Stem surface*.—Glabrous, satiny, matte.

*Stem number*.—Average of 100.

*Internode length*.—Average of 6 cm.

*Branching*.—Basal branches only, no lateral branches.

Foliage description:

*Leaf shape*.—Lanceolate.

*Leaf division*.—Simple.

*Leaf base*.—Cuneate and decurrent at stem.

*Leaf apex*.—Acuminate-like but tapering to a very fine point.

*Leaf aspect*.—Held upright to curved downward.

*Leaf venation*.—Parallel, matches leaf color.

*Leaf margins*.—Entire.

*Leaf attachment*.—Sheathed.

*Leaf size*.—Leaf blade; top leaf an average of 6 mm in width and 13 cm in length, base leaf 2 cm in length, 5 mm in width, sheathed portion; an average of 2 cm in length and 1 mm in width.

*Leaf number*.—Average of 4 per culm.

*Leaf arrangement*.—Alternate.

*Ligule*.—None.

*Leaf surface*.—Both surfaces; matte, glabrous, translucent.

*Leaf color*.—Young opening leaves both surfaces; variegated with vertical streaks of 1A and 155A, mature fully open leaves both surfaces; variegated with vertical streaks of NN155C, 1B and 143B, mature leaves both surfaces; variegated with vertical streaks of 144A, N144A, and NN155B, some of the base leaf apexes flushed with 187B.

Inflorescence description:

*General description*.—Terminal airy panicle of single spikelets.

*Lastingness of inflorescence*.—Each panicle blooms for about 3 weeks, persistent.

*Fragrance*.—None.

*Panicle size*.—Average of 6 cm in length and up to 4 cm in width.

*Panicle number*.—One per culm.

*Rachis*.—An average of 4.5 cm in length (continuous with culm), 0.5 mm in diameter, 143D in color, with rachilla emerging to about a 45° angle to culm.

*Spikelet bud*.—About 6 mm in length and 1 mm in width, narrow lanceolate in shape, 145C to 145D in color.

*Spikelet description*.—Single floret enclosed by one glume and one lemma, glume; lanceolate in shape with a glabrous surface, entire margin, acute apex, 6 mm in length, 1 mm in width and 145D and suffused with 185B in color, lemma; lanceolate in shape with a glabrous surface, entire margin, acute apex, 6.5 mm in length, 1 mm in width and 145D and suffused with 185B in color.

*Spikelet number*.—Average of 60 per panicle.

*Spikelet size*.—About 7 mm in length and 4 mm in width.

Reproductive organs:

*Stamens*.—2, anthers; dorsifixed, x-shaped, 2 mm in length, 187A in color, pollen; not observed.

*Pistils*.—2, 1.5 mm in length, stigmas; fimbriate in shape, 0.5 mm in length, and N77C in color, style; transparent in color, 0.5 mm in length, ovary; 145A in color.

*Seed*.—Seed development has not been observed.

It is claimed:

1. A new and distinct cultivar of *Hakonechloa* plant named 'Hakbri1' as herein illustrated and described.

* * * * *